United States Patent
Periana et al.

(10) Patent No.: US 10,011,547 B2
(45) Date of Patent: Jul. 3, 2018

(54) PROCESS FOR THE FUNCTIONALIZATION OF HETEROALKANES AND ARENES

(71) Applicant: The Scripps Research Institute, La Jolla, CA (US)

(72) Inventors: Roy A. Periana, Jupiter, FL (US); Michael M. Konnick, Palm Beach Gardens, FL (US); Brian G. Hashiguchi, Palm Beach Gardens, FL (US)

(73) Assignee: The Scripps Research Institute, La Jolla, CA (US)

( * ) Notice: Subject to any disclaimer, the term of this patent is extended or adjusted under 35 U.S.C. 154(b) by 0 days.

(21) Appl. No.: 15/506,583

(22) PCT Filed: Aug. 25, 2015

(86) PCT No.: PCT/US2015/046721
§ 371 (c)(1),
(2) Date: Feb. 24, 2017

(87) PCT Pub. No.: WO2016/033061
PCT Pub. Date: Mar. 3, 2016

(65) Prior Publication Data
US 2017/0275222 A1    Sep. 28, 2017

Related U.S. Application Data

(60) Provisional application No. 62/042,101, filed on Aug. 26, 2014, provisional application No. 62/041,270, filed on Aug. 25, 2014.

(51) Int. Cl.
| | |
|---|---|
| *C07C 69/34* | (2006.01) |
| *C07C 29/48* | (2006.01) |
| *C07C 53/18* | (2006.01) |
| *C07C 67/055* | (2006.01) |
| *C07C 67/12* | (2006.01) |
| *C07C 29/72* | (2006.01) |

(52) U.S. Cl.
CPC .............. *C07C 29/48* (2013.01); *C07C 53/18* (2013.01); *C07C 67/055* (2013.01); *C07C 67/12* (2013.01); *C07C 29/72* (2013.01); *C07C 2523/08* (2013.01); *C07C 2523/14* (2013.01); *C07C 2523/16* (2013.01); *C07C 2523/70* (2013.01)

(58) Field of Classification Search
CPC ......... C07C 29/48; C07C 29/72; C07C 53/18; C07C 67/055; C07C 67/12; C07C 2523/08; C07C 2523/14; C07C 2523/16; C07C 2523/70; C07C 51/54; C07C 67/035; C07C 67/05; C07C 69/63; C07C 71/00; Y02P 20/582
See application file for complete search history.

(56) References Cited

U.S. PATENT DOCUMENTS 4,268,689 A * 5/1981 Knifton ................... C07C 67/36
                                                    502/200

OTHER PUBLICATIONS

Hashiguchi et al. (Main-Group Compounds Selectively Oxidize Mixtures of Methane, Ethane, and Propane to Alcohol Esters, Science, vol. 343, pp. 1232-1237, published Mar. 14, 2014) (Year: 2014).*
Konnick et al., "Selective CH Functionalization of Methane, Ethane, and Propane by a Perfluoroarene Iodine(III) Complex," Angewandte Chemie International Edition, 53(39): 10490-10494 (Aug. 11, 2014).
European Patent Office, International Search Report and the Written Opinion in International Application No. PCT/US2015/046721 (dated Nov. 6, 2015).

* cited by examiner

*Primary Examiner* — Jafar Parsa
*Assistant Examiner* — Blaine G Doletski
(74) *Attorney, Agent, or Firm* — Leydig, Voit & Mayer, Ltd.

(57) ABSTRACT

Provided are methods and materials for the functionalization of a heteroalkane or arene using an oxidizing electrophile as a stoichiometric agent or catalyst. The reaction involves the replacement of a hydrogen atom on an sp3-hybridized carbon atom of the heteroalkane or of a hydrogen atom on an sp2-hybridized carbon atom of the arene. A main group element organometallic intermediate is formed that undergoes further conversion to a functionalized heteroalkane or arene.

29 Claims, 2 Drawing Sheets

Cycle 1: A -> C and D -> B
         E -> G and H -> F

Cycle 2: A -> B and D -> C
         E -> F and H -> B

Cycle 3: A -> C and D -> B
         E -> G and H -> F

Cycle 4: A -> B and D -> C
         E -> F and H -> G

Etc.

PROCESS FOR THE FUNCTIONALIZATION OF HETEROALKANES AND ARENES

CROSS-REFERENCE TO RELATED APPLICATIONS

This patent application is a U.S. national phase of International Patent Application No. PCT/US2015/046721, filed Aug. 25, 2015, which claims the benefit of U.S. Provisional Patent Application No. 62/042,101, filed Aug. 26, 2014, and U.S. Provisional Patent Application No. 62/041,270, filed Aug. 25, 2014, the disclosures of which are incorporated in their entirety by reference.

STATEMENT REGARDING FEDERALLY SPONSORED RESEARCH AND DEVELOPMENT

This invention was made with government support under GQ10044-133945 awarded by the U.S. Department of Energy. The Government has certain rights in this invention.

BACKGROUND OF THE INVENTION

An important approach that has emerged in the last few decades is the design of molecular (homogeneous) catalysts or reagents for the oxidative functionalization of hydrocarbons based on the C—H activation reaction. This involves reaction of a regenerable M-X catalyst or reagent (M being a main group element in an oxidized state and X being one or more charge-balancing counterions) with a C—H bond of a hydrocarbon (R—H) under relatively mild conditions to selectively generate an M-R intermediate that can be converted to the desired R—X product with regeneration of M-X (eq.1).

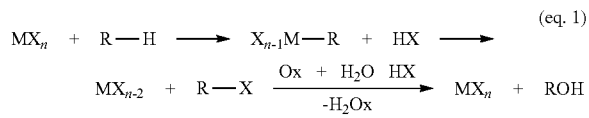

There has been significant effort in this area of research with homogeneous as well as heterogeneous catalysts, and substantial progress has been made in recent years. Most of the work on the homogeneous systems have been primarily based on transition metals (with unfilled d-shells, $d^{<10}$), such as Pt, Pd, Rh, and Ir. In contrast, relatively few studies have been directed toward the classic main group elements with a filled d-shell ($d^{10}$). In 1993, Periana reported an example of a main group, metal cation, $Hg^{II}$, in the superacid solvents, concentrated $H_2SO_4$ and $CF_3SO_3H$, for direct conversion of methane to methanol esters (Periana et al., Science 259, 340-343 (1993)); see also International Patent Application WO 92/14738). In spite of the simplicity of the $Hg^{II}$ system, it was not further developed due to lack of reaction in more practical weaker acid media such as $CF_3CO_2H$ (TFAH or HTFA), $CH_3CO_2H$ (HOAc), or aqueous acids where product separation can be practical. Another key issue was that the reactions of ethane and propane were unselective with the $Hg^{II}$ system.

$Tl^{III}$ was found to be active for methane oxidation to the ester. However, this activity was only examined in superacid media and only with methane. $Tl^{III}$ or $Pb^{IV}$ systems in TFAH or with higher alkanes were not studied primarily due to the recognition that both $Tl^{III}$ ($E°=1.2$ V) and $Pb^{IV}$ ($E°=1.5$ V) are stronger oxidants as well as electrophiles than $Hg^{II}$ ($E°=0.9V$). See, e.g., A. J. Bard, R. Parsons, J. Jordan, Standard Potentials in Aqueous Solution. (International Union of Pure and Applied Chemistry, New York, N.Y., 1985). Consequently, on the basis of the general considerations at that time, these main group cations were understood to be more likely than $Hg^{II}$ to initiate unselective radical reaction with the higher alkanes and to be inhibited by weaker, more nucleophilic acid solvents. This model of expected lack of reactivity of strong electrophiles in weak acid media also seemed consistent with the observation that in earlier work on Pt bipyrimidine complexes, the Pt(II) state was found to active in superacid media whereas the arguably more electrophilic Pt(IV) state was inactive.

There similarly is no direct process for the conversion of benzene to phenol. Phenol is typically made through indirect processes involving addition of propylene, chlorine, etc. A direct process has been challenging because of the low selectivity typically involved in the functionalization of an arene, such as benzene.

Thus, it would be desirable to provide a method to selectively and directly functionalize compounds, such as heteroalkanes and arenes, without the generation of significant amounts of by-products and waste and without the need for an expensive transition metal catalyst.

BRIEF SUMMARY OF THE INVENTION

The invention provides a process of preparing a functionalized compound, comprising:
(a) providing a compound that is a heteroalkane or an arene,
wherein
the heteroalkane comprises at least one $sp^3$-hybridized carbon atom bearing a hydrogen atom and at least one heteroatom other than a carbon or hydrogen atom, and
the arene comprises at least one $sp^2$-hybridized carbon atom bearing a hydrogen, and optionally comprising
(i) one or more $sp^3$-hybridized carbon atoms,
(ii) one or more heteroatoms, or
(iii) both (i) and (ii),
(b) contacting the compound with
(i) an oxidizing electrophile comprising a main group element in oxidized form, or
(ii) an oxidant and a reduced form of the oxidizing electrophile,
to provide an initial reaction product, and
(c) contacting the initial reaction product with a functionalized reactant, wherein a functionalized portion of the functionalized reactant replaces a hydrogen on the initial reaction product to provide the functionalized compound.

DETAILED DESCRIPTION OF THE INVENTION

Figure 1:
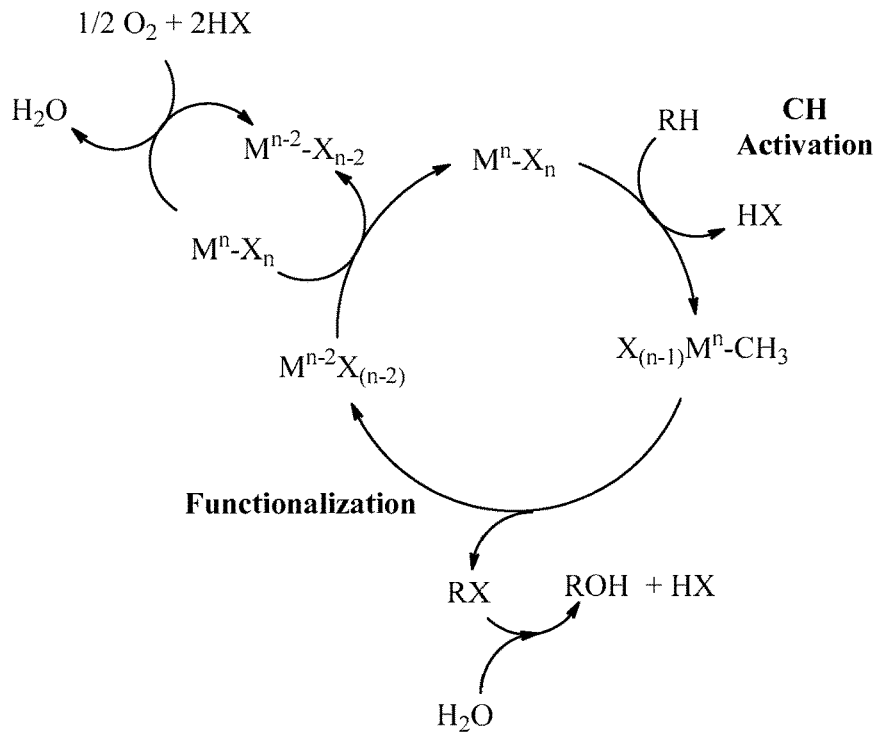
FIG. 1 is a proposed reaction mechanism for the overall conversion of hydrocarbons (RH) to the corresponding phenols (ROH) via the CH activation reaction.

By the methods and compositions disclosed and claimed herein, a viable industrial approach is provided to convert heteroalkanes (e.g., alcohols, esters, halocarbons, carboxylic acids, carboxamides, and the like) and arenes (e.g., aryls and heteroaryls), to C—H bond substitution products, such as hydroxylated, aminated, halogenated, or carbonylated derivatives of the reaction substrate. The reactive main group element (M) in oxidized form (e.g., $MX_n$) can bring about what is believed to be an initial electrophilic C—H bond activation reaction. The reaction can take place by a different mechanism yet yield a product equivalent to the product of C—H bond reaction, e.g., by radical or other mechanisms. After formation of the activated intermediate and conversion to the functionalized heteroalkane or arene, it is possible to recover the reduced form of reagent M for recycling back to the reactive, oxidized state (e.g., $MX_n$). The reactivity of the reagents and methods disclosed and claimed herein allows the process to be carried out without the presence of an expensive or difficult-to-handle superacid, a hitherto unachieved goal. By the discoveries of the inventors described herein, a low-temperature, low-pressure, and sustainable process with in situ or ex situ reagent recycling has been devised that offers an economically and environmentally attractive alternative to previously known processes (e.g., the syngas approach to production of lower alcohols such as methanol from lower alkanes) on an industrial scale.

Accordingly, the invention provides a process of preparing a functionalized compound, comprising:

(a) providing a compound that is a heteroalkane or an arene,
wherein
the heteroalkane comprises at least one sp³-hybridized carbon atom bearing a hydrogen atom and at least one heteroatom other than a carbon or hydrogen atom, and
the arene comprises at least one sp²-hybridized carbon atom bearing a hydrogen, and optionally comprising
(i) one or more sp³-hybridized carbon atoms,
(ii) one or more heteroatoms, or
(iii) both (i) and (ii),
(b) contacting the compound with
(i) an oxidizing electrophile comprising a main group element in oxidized form, or
(ii) an oxidant and a reduced form of the oxidizing electrophile,
to provide an initial reaction product, and
(c) contacting the initial reaction product with a functionalized reactant, wherein a functionalized portion of the functionalized reactant replaces a hydrogen on the initial reaction product to provide the functionalized compound.

The use of oxidizing electrophiles as reagents in non-superacid systems represents a surprising discovery that provides heteroalkane or arene oxidation systems using industrially applicable materials.

In the process, the compound to be functionalized is a heteroalkane or an arene, as described herein.

A "heteroalkane" substrate of the present reaction is a molecule that includes at least one sp³-hybridized carbon atom, in which at least one substituent of that carbon atom is a hydrogen atom such that a C—H bond is present. The alkane portion of the heteroalkane implies a straight-chain or branched alkyl substituent containing from, for example, from about 1 to about 16 carbon atoms (e.g., from about 1 to about 12 carbon atoms, from about 1 to about 10 carbon atoms, from about 1 to about 8 carbon atoms, from about 1 to about 6 carbon atoms, or from about 1 to about 4 carbon atoms). The heteroalkane additionally comprises at least one "heteroatom," i.e., an atom that is not a carbon or a hydrogen. Examples of heteroatoms include atoms of elements such as oxygen, nitrogen, sulfur, a halogen (e.g., chlorine), and/or a metal (e.g., tin). Thus, a heteroalkane substrate as the term is used herein can be, for example, an alkylcarbinol, an alkylamine, a halocarbon, or an organometallic compound. Examples of heteroalkane substrates useful for practice of a method of the invention include alcohols (e.g., n-propanol or n-butanol) and compounds comprising an ether oxygen, an ester, or an amide group. For instance, a method of the invention can be used to provide reaction products of heteroalkanes such as butanol, halobutanes, and butanoyl compounds, such as esters and amides.

A "functionalized" heteroalkane is a derivative of the heteroalkane substrate, in which the sp³-hybridized carbon atom bearing a hydrogen atom undergoes reaction at that C—H bond to produce a functionalized heteroalkane product that comprises the heteroalkane structure but with an sp³-hybridized carbon atom bearing a functional (i.e., non-hydrogen) group. For example, in addition to being oxidized/hydrolyzed to yield the corresponding alkanol, a heteroalkane can undergo other reactions, e.g., to yield amines by reaction with hydrazine or other nitrogen-containing reagents. Other products can be obtained from the initial reaction product, such as products of stannylation, thiolation, phosphinylation, carbonylation, elimination, and/or halogenation reactions.

An "arene," as the term is used herein, refers to an organic compound comprising at least one sp²-hybridized carbon atom bearing a hydrogen atom, in which the arene compound can further comprise (i) one or more sp³-hybridized carbon atoms, (ii) one or more heteroatoms, or (iii) both (i) and (ii). The term "arene" encompasses "aryl" and "heteroaryl" ring systems.

The term "aryl" refers to an unsubstituted or substituted aromatic carbocyclic moiety, as commonly understood in the art, and includes monocyclic and polycyclic aromatics such as, for example, benzene, biphenyl, naphthalen, anthracene, pyrene, and the like. An aryl moiety generally contains from, for example, 6 to 30 carbon atoms, from 6 to 18 carbon atoms, from 6 to 14 carbon atoms, or from 6 to 10 carbon atoms. It is understood that the term aryl includes carbocyclic moieties that are planar and comprise $4n+2\pi$ electrons, according to Hückel's Rule, wherein n=1, 2, or 3. The aryl can be substituted or unsubstituted, as described herein.

The term "heteroaryl" refers to aromatic 5 or 6 membered monocyclic groups, 9 or 10 membered bicyclic groups, and 11 to 14 membered tricyclic groups which have at least one heteroatom (O, S, or N) in at least one of the rings. Each ring of the heteroaryl group containing a heteroatom can contain one or two oxygen or sulfur atoms and/or from one to four nitrogen atoms provided that the total number of heteroatoms in each ring is four or less and each ring has at least one carbon atom. The fused rings completing the bicyclic and tricyclic groups can contain only carbon atoms and can be saturated, partially saturated, or unsaturated. The nitrogen and sulfur atoms can optionally be oxidized, and the nitrogen atoms can optionally be quaternized. Heteroaryl groups which are bicyclic or tricyclic must include at least one fully aromatic ring but the other fused ring or rings can be aromatic or non-aromatic. The heteroaryl group can be attached at any available nitrogen or carbon atom of any ring. Illustrative examples of heteroaryl groups are quinoline, pyridine, pyridazine, pyrimidine, pyrazine, benzimidazole, triazine, imidazole, (1,2,3)- and (1,2,4)-triazole, pyrazine, tetrazole, furan, pyrrole, thiophene, isothiazole, thiazole, isoxazole, and oxadiazole. The heteroaryl can be substituted or unsubstituted, as described herein.

The arene can optionally be substituted with one or more heteroatoms, one or more alkyl groups, and the like. Examples of heteroatoms include atoms of elements such as oxygen, nitrogen, sulfur, a halogen (e.g., chlorine), and/or a metal (e.g., tin), e.g., aryl or heteroaryl alcohols (phenols), alkoxys, esters, amines, thiols, halocarbons, carboxylic acids, and carboxamides. Examples of suitable arene substrates include aryls, such as benzene, naphthalene, phenols, phenolic ethers, derivatives of anilines, haloaryl compounds, and the like. Further examples of suitable arene substrates include heteroaryls, such as pyridine, quinoline, pyrrole, indole, thiophene, and the like. In an embodiment, the arene is benzene, pyridine, quinoline, or naphthalene, each of which is optionally substituted.

A "functionalized" arene is a derivative of the arene substrate, in which the $sp^2$-hybridized carbon atom bearing a hydrogen atom undergoes reaction at that C—H bond to produce a functionalized arene product, i.e., a product that comprises the arene substrate structure but with the $sp^2$-hybridized carbon atom undergoing reaction now bearing a non-hydrogen group. For one possible mechanism, a hydrogen atom on an $sp^2$-hybridized carbon atom can be first replaced by the main group element M from the oxidizing electrophile, and subsequently replaced by a hydroxyl group, an amino group, a halogen, a carboxamido group, a C=O addition product, or the like.

In some embodiments, the compound is a heteroalkane. Preferably, the heteroalkane is an alkyl monoester (e.g., an ester of n-butanol or n-propanol). In a particular embodiment, the compound can be an ester of n-butanol or n-propanol, and the functionalized heteroalkane product can be a diester of 1,4-butanediol or 1,3-propanediol, respectively.

In other aspects, the compound is an arene. Preferably, the arene comprises an aryl ring system and/or the arene comprises a heteroaryl ring system.

In step (b) of the process, the compound to be functionalized (i.e., a heteroalkane or arene) is contacted with (i) an oxidizing electrophile comprising a main group element in oxidized form or (ii) an oxidant and a reduced form of the oxidizing electrophile. In some embodiments, the contacting step (step (b)) comprises contacting the compound with an oxidizing electrophile comprising a main group element in oxidized form. In other embodiments, step (b) comprises contacting the compound with an oxidant and a reduced form of the oxidizing electrophile.

The oxidizing electrophile of any of the methods described herein comprises a main group element. A main group element, as the term is used herein, refers to metals and non-metals, including elements of CAS groups IIIA, IVA, VA, VIA, and VIIA, that are post-transition elements, i.e., being of higher atomic number than the last element of the first transition series, Zn, i.e., of atomic number >30. In an embodiment, the main group element is an element selected from CAS groups IIIA, IVA, VA, and VIA. Thus, an oxidizing electrophile used in practice of methods of the invention includes elements having stable isotopic forms of atomic numbers 31-35, 49-53, and 81-83. In a preferred embodiment, the oxidizing electrophile includes at least one element that is a stable isotopic form of any one of atomic numbers 31-34, 49-52, and 81-83. The main group element, in some embodiments, has a $d^{10}$ electronic configuration. However, an oxidizing electrophile used in practice of a method of the invention can have other than a $d^{10}$ electronic configuration. The main group element can cycle between a higher oxidation state (in the oxidizing electrophile reagent that reacts with the alkane C—H bond) and a lower oxidation state (an electrophile reduction product, from which the oxidizing electrophile can be regenerated, either in situ or in a discrete step). By this means, an economically and environmentally favorable self-contained system for heteroalkane or arene conversion, e.g., to heteroalkane or arene oxygenates, can be formed, consuming only a second oxidant (e.g., hydrogen peroxide, oxygen, or ozone). In an embodiment, the main group element in oxidized form is in an oxidation state of +n. In other embodiments, the main group element is in an oxidation state of +(n−2) or +(n−1) for an electrophile reduction product that is formed by the oxidizing electrophile.

As known in the art, an oxidizing electrophile can be known as a soft oxidizing electrophile. A "soft" electrophile, as the term is used herein, relates to classification under the hard/soft acid/base (HSAB) concept, known as the Pearson acid base concept, which assigns the terms "hard" or "soft" and the terms "acid" or "base" to chemical species. The term "hard" applies to species that are weakly polarizable, whereas the term "soft" applies to species that are strongly polarizable. See R. G. Pearson, Chemical Hardness—Applications From Molecules to Solids, Wiley-VCH, Weinheim, 1997.

Table 1 is a listing of exemplary species based on Pearson hard and soft theory. Oxidizing electrophiles used in practice of methods of the invention are classified as soft according to the HSAB theory, and include forms of main group elements such as Tl, Pb, Bi, Sb, Se, Te, and I. Higher oxidation states of these elements, as salts or compounds thereof, are used as the soft oxidizing electrophiles for practice of methods of the invention.

TABLE 1

Classification of Pearson Hard and Soft Acids

| Hard Acids | Borderline Acids | Soft Acids |
|---|---|---|
| $H^+$, $Li^+$, $Na^+$, $K^+$, $Be^{+2}$, $Mg^{+2}$, $Ca^{+2}$, $Ba^{+2}$, $Sc^{+3}$, $La^{+2}$, $Ce^{+4}$, $Gd^{+3}$, $Lu^{+3}$, $Th^{+4}$, $U^{+4}$, $UO_2^{+2}$, $Ti^{+4}$, $Zr^{+4}$, $Hf^{+4}$, $VO^{+2}$, $Cr^{+3}$, $BF_3$, $BCl_3$, $Al^{+3}$, $AlCl_3$, $CO_2$, $RCO^+$, $NC^+$, $Si^{+4}$, $Sn^{+4}$ | $Fe^{+2}$, $Co^{+2}$, $Ni^{+2}$, $Zn^{+2}$, $Rh^{+3}$, $Ir^{+3}$, $Ru^{+3}$, $Os^{+3}$, $B(CH_3)_3$, $GaH_3$, $R_3C+$, $C_4H_5+$, $Sn^{+2}$, $Pb^{+2}$, $NO^+$, $Sb^{+3}$, $Bi^{+3}$, $SO_2$ | $Pd^{+2}$, $Pt^{+2}$, $Pt^{+4}$, $Cu^+$, $Ag^+$, $Au^+$, $Cd^{+2}$, $Hg^+$, $Hg^{+2}$, $Tl^{+3}$, $Ph^{+4}$, $Bi^{+5}$, $Br^+$, $Br_2$, $I^+$, $I_2$, $Se^{+6}$, $Te^{+6}$, $I^{+3}$ |

Other soft acids are known to those of skill in the art, and elements having suitable pairs of oxidation states can be selected by the person of skill in the art for practicing the methods of the invention.

In some embodiments, the oxidizing electrophile comprises a main group element selected from thallium, lead, bismuth, antimony, selenium, tellurium, iodine, and a mixture thereof, each of which is in oxidized form. In a particular embodiment, the oxidizing electrophile comprises a main group element selected from thallium, lead, bismuth, antimony, selenium, tellurium, and a mixture thereof, each of which is in oxidized form. In the case of Hg, Tl, and Pb, the oxidized forms that are most active are those that have the electronic configuration of Xe, $5d^{10}$, $6s^0$. However, this need not be the electronic configuration of systems that react since I(III), with an electronic configuration of Kr, $4d^{10}$, $5s^2$, $5p^2$, is found to be active for CH activation. In particular embodiments, the oxidizing electrophile can comprise thallium(III), lead(IV), bismuth(V), iodine(III), Sb(V), iodine (V), or a mixture of any of the foregoing elements. In a preferred embodiment, the oxidizing electrophile comprises thallium(III), lead(IV), bismuth(V), Sb(V), or any mixture thereof. In an embodiment, the oxidizing electrophile comprises thallium(III). In another embodiment, the oxidizing electrophile comprises lead(IV). In yet another embodiment, the oxidizing electrophile comprises bismuth(V). In still yet another embodiment, the oxidizing electrophile comprises Sb(V).

In some embodiments, the oxidizing electrophile comprising a main group element in oxidized form is a salt, wherein the counterion of the main group element in oxidized form is a conjugate anion of an acid (e.g., one or more trifluoroacetate, acetate, sulfate, and/or alkylsulfonate anions). For example, the oxidizing electrophile can have the formula $M^{+n}X_n$, in which M is a metal or non-metal main group element cation in an oxidation state of n, X is an anionic counterion, and n is the number of anionic charges necessary to balance the n+ positive charge of the metal ion. The anionic counterion (X) is any suitable anionic counterion/ligand that enables the formation of an electrophile reduction product, such as, for example, an eletrophile reduction product that comprises one or more trifluoroacetate, acetate, sulfate, and/or alkylsulfonate anions. Without wishing to be bound by any particular theory, the inventors believe that $M^{+n}X_n$ undergoes a reaction with the heteroalkane or arene to yield an electrophile reduction product of formula $M^{+(n-2)}X_{n-2}$ or $M^{+(n-1)}X_{n-1}$. Preferably, such reaction takes place in an acidic medium as described herein.

In an embodiment of any of the processes described herein, the reaction of the reactive main group element with the compound to be functionalized (i.e., a heteroalkane or arene) (e.g., step (b)) is carried out in an acidic medium, including an aqueous acidic medium. The acidic acid is any suitable acid, such as a mineral acid, a carboxylic acid, a sulfonic acid, aqueous solutions thereof, or any combination thereof. The acidic medium preferably comprises an oxygen acid, e.g., trifluoroacetic acid, acetic acid, methanesulfonic acid, or aqueous solutions thereof. If desired, the acidic medium can be recycled. Without wishing to be bound by theory, the inventors believe that an activated $X_{(n-1)}$M-R initial reaction product is formed, in which the main group element substitutes an H of a C—H bond of the heteroalkane or arene, possibly by an electrophilic process. It was surprisingly discovered that using the compositions and methods disclosed herein, efficient reaction of a heteroalkane or arene can be achieved without the presence of a superacid, and under relatively mild conditions, e.g., under 300° C., preferably under 200° C., to provide the activated intermediate (initial reaction product).

This activated intermediate $X_{(n-1)}$M-R, wherein R is the heteroalkane or arene substrate in which a hydrogen atom of an sp$^3$-hybridized carbon atom of the heteroalkane or a hydrogen atom of an sp$^2$-hybridized carbon atom of the arene, respectively, has been replaced by atom M, can then undergo reaction with the solvent milieu, e.g., with an acid such as trifluoroacetic acid, acetic acid, methanesulfonic acid, and the like, to provide as an isolable product R—X, i.e., a functionalized heteroalkane or arene. For example, a heteroalkyl oxygenate, e.g., a heteroalkyl ester such as a trifluoroacetate, heteroalkyl acetate, heteroalkyl methanesulfonate, and the like, respectively, can be formed. The functionalized heteroalkyl ester can then be further hydrolyzed to yield a functionalized heteroalkane product wherein the hydrogen atom of an sp$^3$-hybridized carbon atom has been replaced by a hydroxyl group. A similar mechanism is envisioned for an arene substrate, in which a hydrogen atom of an sp$^2$-hybridized carbon atom of the arene has been preferentially functionalized over a hydrogen atom of an sp$^3$-hybridized carbon atom. Other products can be obtained from the activated intermediate (e.g., $X_{(n-1)}$M-R) compounds, such as products of amination, stannylation, thiolation, phosphinylation, carbonylation, elimination, or halogenation reactions.

The invention can provide methods of heteroalkane or arene oxidation or functionalization that do not require the use of superacids, although in various embodiments, superacids can be employed effectively to achieve the desired conversion. A superacid, as the term is used herein is an acid with an acidity greater than or equal to that of concentrated sulfuric acid, which has a Hammett acidity function ($H_0$) of −12. Commercially available superacids include concentrated sulfuric acid, as well as trifluoromethanesulfonic acid ($CF_3SO_3H$) and fluorosulfuric acid ($HSO_3F$), both of which are about a thousand times stronger (i.e., have more negative $H_0$ values) than concentrated sulfuric acid.

The advantages of avoiding the use of superacids in the processes of the invention include lower cost, less stringent construction material demands for reactors, increased stability of products from higher alkanes, and ease of recycling the acidic component of the reaction milieu. Superacids can have a very high affinity for water, so any process that involves re-concentration of a superacid from water would incur prohibitively high energy costs for water removal.

The invention thus provides improvements over the previously disclosed process employing superacids, because acid solvents weaker than 98% sulfuric acid can be used, such as trifluoroacetic acid, acetic acid, methanesulfonic acid, phosphoric acid, aqueous mineral acids or organic acids, and the like, including aqueous solutions thereof. In the previously disclosed mercury system, or the (bpym)PtX$_2$ system, very strong acids (superacids), such as 98% sulfuric acid or $CF_3SO_3H$, were required. These systems were presumed to operate by electrophilic mechanisms. Consistent with that presumption, both systems were found to be inactive in weaker, more nucleophilic acid solvents such as $CF_3CO_2H$ or acetic acid. It was also proposed that a free-radical mechanism could be involved in the Hg(II) system as the Hg(II) was strongly oxidizing. The foregoing information suggests that stronger electrophiles and oxidants, such as Tl(III), Pb(IV), Bi(V), etc., would be less active and selective than the less electrophilic systems based on Hg(II) or Pt(II). Indeed, the observation that (bpym)Pt(IV) is inactive in weaker acids also appears to support this electrophilic inhibition model. As a result no work appears to have been reported on the use of main group cations for alkane oxidation since the reports of the Hg(II) systems in 1993.

Interestingly, studies show that the rates of water exchange with powerful electrophiles such as Hg(II) and Tl(III) can be as large as $10^{20}$ times that for electrophiles such as Ir(III), Pt(II), and Pt(IV) (F. Basolo, R. G. Pearson, Mechanisms of Inorganic Reactions (Wiley, New York, ed. 2, 1967)). This effect can be conceptually attributed to the lack of Ligand Field Stabilization Energies (LFSEs) for cations with $d^{10}$ electronic configurations such as Hg(II) and Tl(III) and high LFSE's for cations with $d^{<10}$. Counterintuitively, these high exchange rates for strong $d^m$ electrophiles such as Hg(II), Tl(III), Pb(IV), and Bi(V) suggested to the inventors that the expected correlation between increasing electrophilicity and reduced rates of C—H activation may be incorrect. Indeed, studies by the inventors show that increasing electrophilicity actually increases the rate of C—H activation in the $d^{10}$ cations with Pb(IV)>Tl(III)>>Hg(II) (Hashiguchi et al., Science, 343, 1232 (2014)). This relationship is interesting because it suggests that $Hg^{II}$ did not react in $CF_3CO_2H$ in the earlier 1993 studies because the electrophilicity is not sufficiently high. This very important observation by the inventors suggests that other inexpensive, abundant post-transition metal cations can be designed for the activation and functionalization of alkanes in non-superacidic media. Given the low toxicity and common use of bismuth, iodine, antimony, etc., the design of homogeneous systems based on these cations is particularly attractive.

In any of the embodiments described herein, the inventive process can further comprise separating the functionalized compound and an electrophile reduction product that is formed by the oxidizing electrophile.

In any of the embodiments described herein, the reactive main group element by-product from the functionalization reaction is in a reduced state relative to the reagent used in the initial step and can be recovered and recycled back to its reactive, oxidized state. For example, the electrophile reduction product can be contacted with an oxidizing regeneration reagent to regenerate the oxidizing electrophile. The oxidizing regeneration reagent preferably comprises a peroxide (e.g., hydrogen peroxide), oxygen, ozone, nitric acid, or a halogen (e.g., chlorine). If the reaction is carried out in the presence of an oxidant (e.g., $O_2$ or $H_2O_2$), the reduced form can be reoxidized in situ, and the reactive main group element would operate as a catalyst. In an embodiment, the oxidizing regeneration reagent is present in at least stoichiometric quantities relative to the heteroalkane or arene. In another aspect, the oxidizing electrophile comprising a main group element in oxidized form is present in less than stoichiometric quantities relative to the heteroalkane or arene and acts as a catalyst.

In some embodiments, the electrophile reduction product and the oxidizing regeneration reagent are contacted in the presence of an oxidative regeneration catalyst. The oxidative regeneration catalyst can comprise, for example, copper, silver, iron, or vanadium. In some embodiments, when an oxidative regeneration catalyst is used, the oxidizing regeneration reagent is present in at least stoichiometric quantities relative to the heteroalkane or arene. In other embodiments, no oxidizing regeneration reagent is present with the oxidizing electrophile comprising a main group element in oxidized form, and the oxidizing electrophile is present in at least stoichiometric quantities relative to the heteroalkane or arene. In such embodiments, the electrophile reduction product can be oxidized back to the oxidizing electrophile in a discrete step, such as in a two-reactor system that cycles between compound functionalization and oxidizing electrophile regeneration with the second oxidant, as described herein.

In order to provide a functionalized compound, such as a functionalized heteroalkane or functionalized arene, an initial reaction product formed by contacting a heteroalkane or arene with an oxidizing electrophile is contacted with a functionalized reactant. A functionalized portion of the functionalized reactant replaces a hydrogen on the initial reaction product to provide the functionalized compound (e.g., step (c)). The functionalized reactant is any suitable reagent that enables the formation of a functionalized compound. For example, the functionalized reactant can be an oxygen acid, a hydrazine, a hydroxylamine, ammonia, a primary amine, a secondary amine, a stannous salt, octasulfur, alkylthiol, a phosphine, a weak base, formaldehyde, carbon monoxide, or a halide. In a preferred embodiment, the functionalized reactant is an oxygen acid, and step (c) can be described as an oxidation step.

If necessary, step (c) can further comprise contacting the initial reaction product and functionalized reactant with water, an oxidant, or both. The oxidant can be any suitable reagent, such as oxygen, ozone, or a peroxide (e.g., hydrogen peroxide).

Without wishing to be bound by any particular theory, the inventors consider that one possible reaction mechanism for the conversion of a heteroalkane or arene, RH, to its corresponding hydroxylated functionalized product, ROH, is the reaction mechanism shown in FIG. 1. A proposed mechanism for the three-step process is set forth in Scheme 1.

Scheme 1: Conversion of Heteroalkane or Arene (RH) to Hydroxylated Product (ROH)

$$RH + M^n X_n \rightarrow RX + HX + M^{(n-2)} X_{n-2} \qquad (eq.\ 2)$$

$$M^{(n-2)} X_{n-2} + 2HX + \tfrac{1}{2} O_2 \rightarrow MX_n + H_2O \qquad (eq.\ 3)$$

$$RX + H_2O \rightarrow ROH + HX \qquad (eq.\ 4)$$

NET: $RH + \tfrac{1}{2} O_2 \rightarrow ROH$

In one embodiment of this invention, an oxidizing material, $MX_n$, is reacted with a heteroalkane or arene (RH) to selectively generate a functionalized product (RX) and the reduced form of the oxidants, $MX_{n-2}$, as shown in eq. 2. The functionalized product, RX, is selected to minimize over oxidation to undesirable products such as $CO_2$. As it is desirable to use oxygen as the overall oxidant, the reduced form of the oxidant, $MX_{n-2}$, can be regenerated with oxygen from air, as shown in eq. 3. As shown in eq. 4, RX can be hydrolyzed to the corresponding alcohol, ROH. The net reaction is the overall conversion of the heteroalkane or arene (RH) to the corresponding hydroxylated product, ROH. It is possible to carry out the reaction in eq. 2 without a catalyst if the reaction of $MX_n$ with the heteroalkane or arene is facile. However a catalyst can also be utilized. The use of $MX_n$ salts as an air-recyclable stoichiometric oxidizing reagent without the need for catalysts can be advantageous to minimize the complexity of the system and the requirement to identify separate catalysts and oxidants that are compatible for reaction with heteroalkanes and/or arenes. Scheme 1 does not represent the only possible reaction scheme. For example, combinations of equations 2 and 4 or equations 2 and 3 or equations 1, 2, and 3 are possible in one reaction or reactor. However, in order to maximize selectivity, safety, and reduce costs, the three steps shown in Scheme 1 can be separately conducted. Other oxidants, such as hydrogen peroxide, can be used in place of oxygen.

Four criteria can be utilized for identifying suitable $MX_n$ materials for eq. 2 in Scheme 1: (A) good oxidants, wherein $MX_n + 2e^- + 2H^+ \rightarrow MX_{n-2} + 2HX$, $E° \approx \leq -0.5$ V; (B) form relatively strong covalent bonds to carbon; (C) strongly electrophilic; and (D) form relatively weak bonds to the counter anions, X. Species with these characteristics can be described as oxidizing electrophiles (e.g., "soft" oxidizing electrophiles).

Using a specific oxidant, $Tl(CF_3CO_2)_3$, as an example, a mechanism of hydroxylating a heteroalkane or arene (RH) is proposed in Scheme 2.

Scheme 2

$Tl(CF_3CO_2)_3 + RH \rightarrow Tl(CF_3CO_2) + CF_3CO_2R + CF_3CO_2H$ (eq. 5)

$Tl(CF_3CO_2) + \tfrac{1}{2}O_2 + 2CF_3CO_2H + Tl(CF_3CO_2)_3 + H_2O$ (eq. 6)

$CF_3CO_2R + H_2O \rightarrow ROH + CF_3CO_2H$ (eq. 7)

NET: $RH + \tfrac{1}{2}O_2 \rightarrow ROH$

Figure 2:
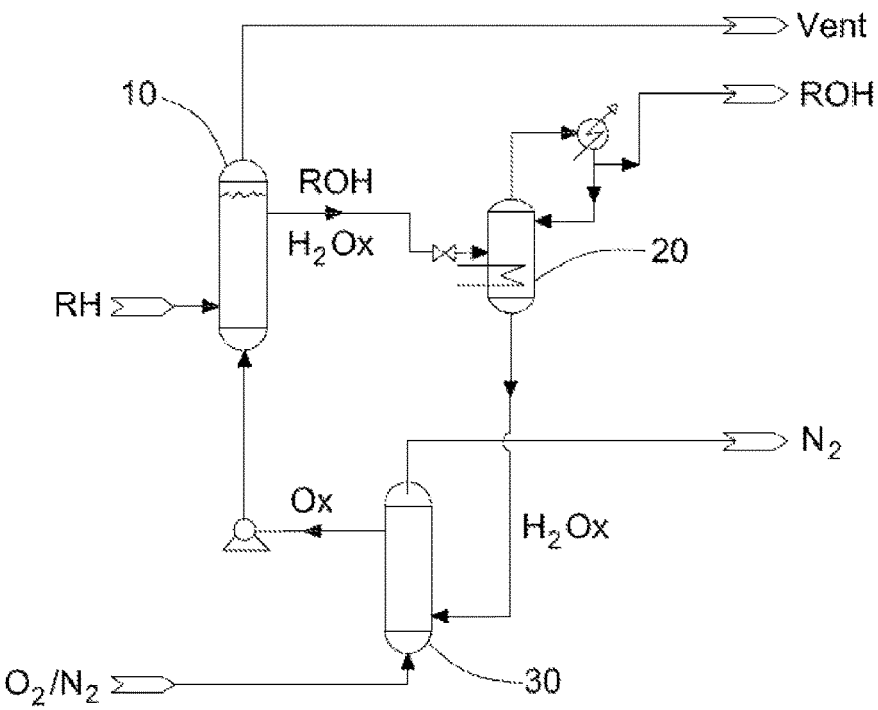
FIG. 2 is an example of the simplified process flow diagram for the continuous partial oxidation of a heteroalkane or arene (RH) to ROH with air.

FIG. 2 is a process design of a continuous reactor system using inexpensive gas-liquid bubble column reactors. Correlating the system of FIG. 2 to the proposed mechanism of Scheme 2, Ox is $Tl(CF_3CO_2)_3$, $H_2Ox$ is $Tl(CF_3CO_2)$, and eq. 5 and eq. 7 of Scheme 2 are combined in the Hydrocarbon Oxidizer reactor (10). The final product ROH is separated from $H_2Ox$ in the ROA Flash Separator (20). Ox and $H_2Ox$ are circulated between the Hydrocarbon Oxidizer (20) in the Oxidant Regenerator (30).

Figure 3:
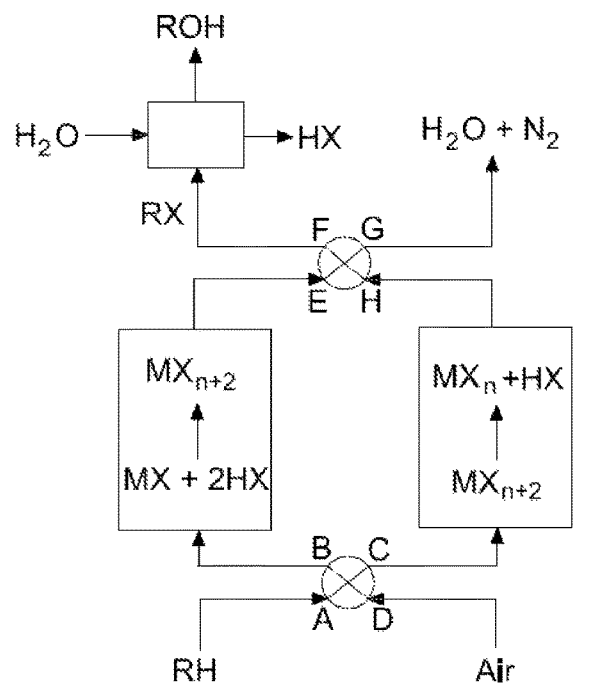
FIG. 3 is a simplified process diagram for the conversion of a heteroalkane or arene (RH) to the corresponding alcohol (ROH) using $MX_n$ as the air recyclable stoichiometric oxidant in a switching reactor system that can continuously generate products.

Another plausible process design using Ox as an air-regenerable stoichiometric reagent is shown in FIG. 3. A central aspect of this scheme is the use of two parallel reactors where the heteroalkane or arene (RH) and oxygen (½ $O_2$) reactants are switched between the two reactors in order to allow for continuous processing. Such a process design can be utilized if pumping between the two reactors is not feasible. The process can be initiated with the reactants directed to the reactors depicted in FIG. 3 as follows, A→C, D→B, E→G, and H→F (Cycle 1). The conversion of the heteroalkane or arene to the desired product by reaction with the oxidant, $MX_n$, can be carried out in one reactor simultaneously with the regeneration of the reduced form of the oxidant, $MX_{n-2}$, by air in the other reactor. After reacting with the heteroalkane or arene, the oxidant, $MX_n$, is converted to the reduced form, $MX_{n-2}$. Simultaneously with this process, the reduced form, $MX_{n-2}$, is oxidized with air to the oxidant, $MX_n$. Switching the heteroalkane or arene and air feeds to the reactors allows for a continuous process for the conversion of the heteroalkane or arene and air to the corresponding alcohol. In one embodiment of these actions, the solvent can be the corresponding acid, HX, of the anion, X. However, the reaction can be run with other solvents or potentially even as highly dispersed solids. FIG. 3 provides examples of alternative suitable cycles:

Cycle 1: A→C and D→B
    E→G and H→F
Cycle 2: A→B and D→C
    E→F and H→G
Cycle 3: A→C and D→B
    E→G and H→F
Cycle 4: A→B and D→C
    E→F and H→G
Etc.

Specific examples of the functionalization of heteroalkanes and arenes are outlined below.

Di-functionalized alkanes such as 1,4-butane diol or 1,3-propane diol are highly valuable materials. As is apparent from Schemes 3 and 4 below, the syntheses of these materials involve multiple steps starting from simple alkanes. These syntheses are very expensive processes that are capital and energy intensive and generate excessive emissions.

Scheme 3. Commerical synthesis of 1,4-butane diol

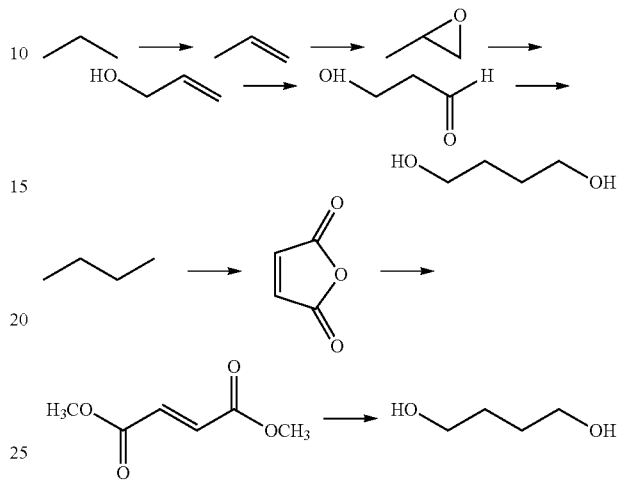

Scheme 4. Commercial synthesis of 1,3-propane diol

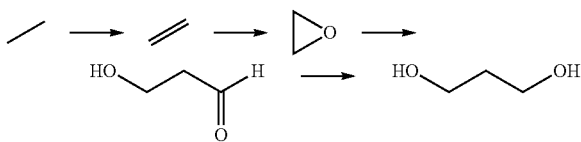

Processes that directly convert the alkanes to these diols in fewer steps that require less energy and capital are substantially cleaner and less expensive. For example, the conversion of alkanes to the corresponding alcohols via a CH activation reaction provide such processes show in Scheme 5.

Scheme 5. Synthesis of
1,4-butane diol and 1,3-propane diol by direct oxygenation

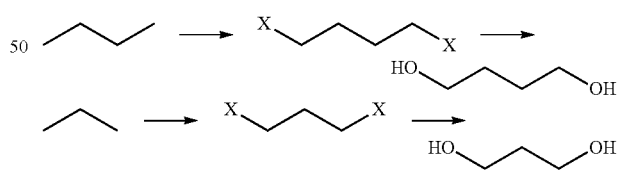

Several potentially practical systems based on main group cations such as $TlX_3$, $PbX_4$, $IX_3$, etc. have been reported for conversions of unsubstituted alkanes (Hashiguchi, et al., *Science,* 343, 1232 (2014) and references therein; and Konnick et al., *Angew. Chem. Int. Ed.,* 53, 10490-10494 (2014) and references therein). A key aspect of these main group systems is that the reactions proceed via electrophilic CH activation and generate oxy-esters in high regioselectivity from the corresponding oxy-acid solvent. The primary reason for this result is that the ester groups, e.g., $CF_3CO_2—$, of the corresponding acid, e.g., $CF_3CO_2H$, are electron withdrawing. Thus, the α-CH bonds of the oxy-ester, e.g., $CF_3CO_2$—$CH_3$, are much less reactive to the electrophilic CH activation reaction than the CH bonds of the parent alkane $CH_4$. This effect can lead to highly selective reactions.

In addition to α-CH bonds, β-CH bonds are less reactive. However, this "protection" effect is attenuated as the number of bonds between the CH bond undergoing reaction and the ester group increases. Thus, the relative reactivity of CH bonds relative to the ester group increases in the order α<β<γ<δ<ε, etc. Depending on the relative rates of these reactions, this effect can be utilized for the synthesis of 1,3-propane diol or 1,4-butane diol. Thus, as shown in Scheme 6, the reaction of n-butyl TFA ester, X=TFA=$CF_3CO_2$ selectively generates the 1,4-diester.

Scheme 6: Functionalization of a heteroalkane according to a method of the invention

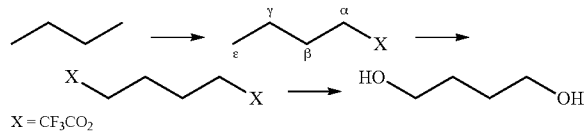

X = $CF_3CO_2$

Figure 4:
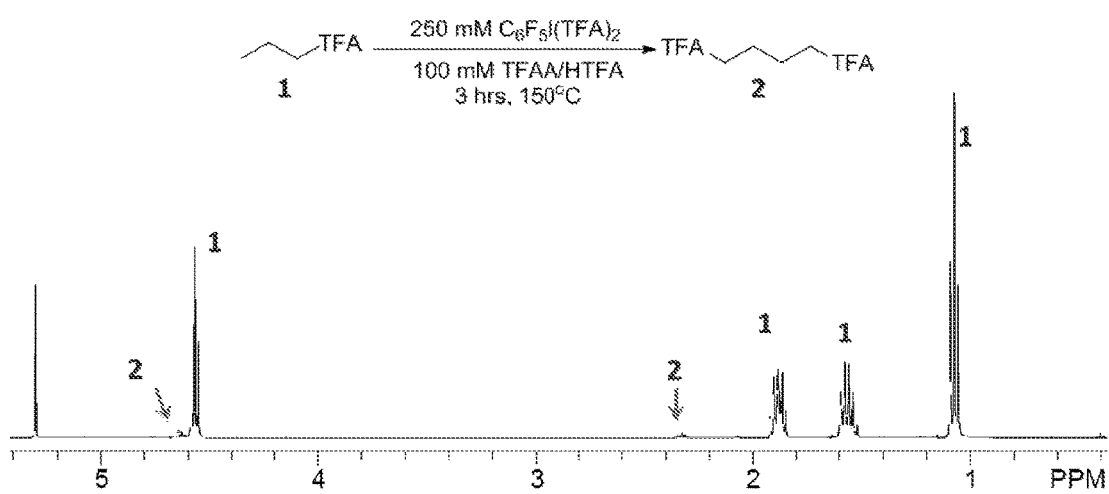
FIG. 4 is a nuclear magnetic resonance (NMR) spectrum showing the results of the reaction of n-butyl TFA with $C_6F_5I(TFA)_2$.

It has been previously demonstrated experimentally that this is the case. $C_6F_5I(TFA)_2$ can selectively convert alkanes (RH) into the corresponding TFA-esters with high selectivity (Konnick et al., *Angew. Chem. Int. Ed.*, 53, 10490-10494 (2014) and references therein). FIG. 4 shows the NMR spectrum of the crude reaction mixture from the reaction of n-butyl TFA, 1, with $C_6F_5I(TFA)_2$ in HTFA. As can be seen, the only material 2 generated in the reaction is the 1,4-diester of 1,4-butane diol. Thus, the inventors unexpectedly discovered that a regioselective functionalization of a heteroalkane, such as an alkyl ester, to yield an alkyl diester, selectively functionalized on a carbon atom distantly disposed on the alkyl chain from the ester group can be provided. A similar reaction has been applied to an arene substrate.

Thus, in certain embodiments, a C—H bond activation reactive intermediate can be contacted with a functionalized reactant that is an oxygen acid (e.g., trifluoroacetic acid, acetic acid, methanesulfonic acid, aqueous solutions thereof, and combinations thereof). The functionalized compound can, if necessary, by hydrolyzed to form the desired final product, such as an alcohol or diol.

In addition to alcohols and diols, a similar reaction sequence can be used to generate amino alcohols, such as ethanolamine or propanolamines, starting with the amine compounds as precursors.

A C—H bond activation reactive intermediate can be used to prepare amine derivatives of the starting heteroalkane or arene, by contacting the initial reaction product with a nitrogen-containing functionalized reactant, such as hydrazine, hydroxylamine, ammonia, ammonia, a primary or secondary amine, or an equivalent. The hydrazine or hydroxylamine reagents can be unsubstituted or can be substituted, e.g., with alkyl or aryl groups, or the like. The reaction of the C—H bond activation reactive intermediate with the nitrogen-containing functionalized reactant can be carried out in situ, or can be carried out on a separated product stream, e.g., following a liquid-liquid extraction. The electrophile reduction product can be recovered and recycled by an oxidative step, and the amine derivative of the starting heteroalkane or arene can be recovered and further purified, further reacted, or both.

The C—H bond activation reactive intermediate can be converted to an organotin (stannane) compound by reaction of the initial reaction product with a stannylation functionalized reactant, such as a stannous salt in the presence of an oxidant. Organotin compounds are known as versatile synthetic intermediates in a variety of reactions.

In some embodiments, the C—H bond activation reactive intermediate can be treated with a sulfur-containing functionalized reactant, such as $S_8$ or an alkylthiol, to provide a thiolated heteroalkane or arene. The organosulfur product obtained can be a thiol, a disulfide, or a thioether. Such compounds can be further converted to sulfoxides and sulfones by oxidation of the sulfur atom.

In further embodiments, the C—H bond activation reactive intermediate can be further processed to provide a carboxamido derivative corresponding to the starting heteroalkane or arene. For instance, the initial reaction product can undergo reaction with a formylation reagent such as formaldehyde and an amine, optionally in the presence of an oxidant, to yield a homologated derivative of the starting heteroalkane or arene with a pendant carboxamido group, wherein an additional carbon atom has been added to the substrate molecule.

The C—H bond activation reactive intermediate can undergo a subsequent reaction with a phosphine to provide a phosphinylated heteroalkane or arene corresponding to the starting material. Use of a trisubstituted phosphine can provide a phosphonium salt, while use of a mono- or disubstituted phosphine can provide the analogous phosphine derivative.

The C—H bond activation reactive intermediate of a heteroalkane can be caused to undergo an elimination reaction, yielding a heteroalkene, by treatment with a very weak base (e.g., a conjugate base of a weak acid, including acetate and trifluoroacetate). The resulting heteroalkene can then be epoxidized, converted to a glycol, and the like.

Carbonylation of the C—H bond activation reactive intermediate, such as with carbon monoxide, can provide an acyl compound that is a homolog of the starting heteroalkane or arene, having added an additional carbon atom. The acyl compound obtained, e.g., an aldehyde, carboxylic acid, or carboxamide, depending upon reaction conditions, can undergo further transformations, such as are well-known in the art.

The C—H bond activation reactive intermediate can undergo a halogenation reaction to provide a halocarbon derivative of the starting heteroalkane or arene, such as by the use of a halide and an oxidant as described herein (e.g., $O_2$).

The functionalization reaction (e.g., step (c)) can be carried out using any suitable conditions. For example, a reactor that is separate from the reactor used for contacting the heteroalkane or arene with the oxidizing electrophile can be used, which allows the secondary reaction to be isolated from the reagents present in the initial reactor. At this stage, the electrophile reduction product can be recovered and recycled in an oxidative process, as described herein, to regenerate the oxidizing electrophile reagent in the high oxidation state needed to carry out the functionalization reaction (e.g., step (c)).

The invention is further illustrated by the following embodiments.

(1) A process of preparing a functionalized compound, comprising:

(a) providing a compound that is a heteroalkane or an arene, wherein the heteroalkane comprises at least one $sp^3$-hybridized carbon atom bearing a hydrogen atom and at least one heteroatom other than a carbon or hydrogen atom, and the arene comprises at least one $sp^2$-hybridized carbon atom bearing a hydrogen, and optionally comprising (i) one or more $sp^3$-hybridized carbon atoms, (ii) one or more heteroatoms, or (iii) both (i) and (ii), (b) contacting the compound with (i) an oxidizing electrophile comprising a main group element in oxidized form, or (ii) an oxidant and a reduced form of the oxidizing electrophile, to provide an initial reaction product, and (c) contacting the initial reaction product with a functionalized reactant, wherein a functionalized portion of the functionalized reactant replaces a hydrogen on the initial reaction product to provide the functionalized compound.

(2) The process of embodiment (1), wherein step (b) comprises contacting the compound with an oxidizing electrophile comprising a main group element in oxidized form.

(3) The process of embodiment (1), wherein step (b) comprises contacting the compound with an oxidant and a reduced form of the oxidizing electrophile.

(4) The process of any one of embodiments (1)-(3), wherein the oxidizing electrophile comprises thallium, lead, bismuth, antimony, selenium, tellurium, or a mixture thereof, each of which is in oxidized form.

(5) The process of embodiment (4), The process of any one of claims 1-3, wherein the oxidizing electrophile comprises iodine in oxidized form, preferably iodine(III) or iodine(V).

(6) The process of any one of embodiments 1-4, wherein the oxidizing electrophile comprises iodine in oxidized form, preferably iodine(III) or iodine(V).

(7) The process of any one of embodiments (1)-(6), wherein the oxidizing electrophile is a salt that includes a counterion of the main group element in oxidized form, and wherein the counterion is a conjugate anion of an acid.

(8) The process of any one of embodiments (1)-(7), wherein the main group element in oxidized form is in an oxidation state of +n, and wherein, for an electrophile reduction product that is formed by the oxidizing electrophile, the element is in an oxidation state of +(n−2) or +(n−1).

(9) The process of any one of embodiments (1)-(8), wherein the oxidizing electrophile is of formula $M^{+n}X_n$, wherein M is a metal or non-metal main group element cation in an oxidation state of n, X is an anionic counterion, and n is the number of anionic charges necessary to balance the n+ positive charge of the metal ion.

(10) The process of embodiment (9), wherein the oxidizing electrophile of formula $M^{+n}X_n$ undergoes reaction with the heteroalkane or arene to yield an electrophile reduction product of formula $M^{+(n-2)}X_{n-2}$ or $M^{+(n-1)}X_{n-1}$.

(11) The process of any one of embodiments (1)-(10), wherein the oxidizing electrophile comprises one or more trifluoroacetate, acetate, sulfate, or alkylsulfonate anions.

(12) The process of any one of embodiments (1)-(11), wherein the contacting of step (b) takes place in an acidic medium.

(13) The process of embodiment (12), wherein the acidic medium is an aqueous acidic medium.

(14) The process of embodiment (12) or embodiment (13), wherein the acidic medium comprises a mineral acid, a carboxylic acid, a sulfonic acid, or any combination thereof.

(15) The process of any one of embodiments (1)-(14), further comprising separating the functionalized compound and an electrophile reduction product that is formed by the oxidizing electrophile.

(16) The process of embodiment (15), further comprising contacting the separated electrophile reduction product and an oxidizing regeneration reagent to regenerate the oxidizing electrophile, wherein the oxidizing regeneration reagent preferably comprises hydrogen peroxide, oxygen, ozone, nitric acid, or a halogen.

(17) The process of embodiment (16), wherein the electrophile reduction product and the oxidizing regeneration reagent are contacted in the presence of an oxidative regeneration catalyst, wherein the oxidative regeneration catalyst preferably comprises copper, silver, iron, or vanadium.

(18) The process of embodiment (17), wherein the oxidizing regeneration reagent is present in at least stoichiometric quantities relative to the compound.

(19) The process of any one of embodiments (1)-(18), wherein the oxidizing electrophile comprising a main group element in oxidized form is present in less than stoichiometric quantities relative to the heteroalkane or arene and acts as a catalyst.

(20) The process of any one of embodiments (1)-(15), wherein no oxidizing regeneration reagent is present with the oxidizing electrophile comprising a main group element in oxidized form, and the oxidizing electrophile is present in at least stoichiometric quantities relative to the compound.

(21) The process of any one of embodiments (1)-(20), wherein step (c) further comprises contacting the initial reaction product and functionalized reactant with water, an oxidant, or both.

(22) The process of any one of embodiments (1)-(21), wherein the functionalized reactant is selected from the group consisting of an oxygen acid, a hydrazine, a hydroxylamine, ammonia, a primary amine, a secondary amine, a stannous salt, octasulfur, alkylthiol, a phosphine, a weak base, formaldehyde, carbon monoxide, and a halide.

(23) The process of any one of embodiments (1)-(22), wherein the compound is a heteroalkane.

(24) The process of embodiment (23), wherein the heteroalkane is an alkyl monoester.

(25) The process of embodiment (24), wherein the heteroalkane is an ester of n-butanol or n-propanol, and the functionalized heteroalkane product is a diester of 1,4-butanediol or 1,3-propanediol, respectively.

(26) The process of any one of embodiments (1)-(22), wherein the compound is an arene.

(27) The process of embodiment (26), wherein the arene comprises an aryl ring system.

(28) The process of embodiment (26), wherein the arene comprises a heteroaryl ring system.

The following examples further illustrate the invention but, of course, should not be construed as in any way limiting its scope.

Example 1

This example demonstrates the use of an oxidizing electrophile comprising a main group element in oxidized form to activate and functionalize a C—H bond of the arene benzene.

$C_6F_5I^{(+3)}(TFA)_2$ (1) was found to be effective for the selective mono-functionalization of benzene (PhH) to PhTFA at lower temperatures (125° C.). Reducing the temperature of this reaction to 100° C. resulted in the complete consumption of 1 with the generation of a new species in solution that was tentatively identified by $^1$H- and $^{19}$F-NMR as the diaryl-$\lambda^3$-iodane $[C_6F_5—I^{III}—C_6H_5][TFA]$ (3) with only trace levels of PhTFA and $C_6F_5—I^I$ (2) observed. Further heating of this solution at 125° C. resulted in the complete conversion of 3 into PhTFA and 2. This observation is consistent with 3 as an intermediate in the conversion of PhH to PhTFA (Scheme 7).

Scheme 7.

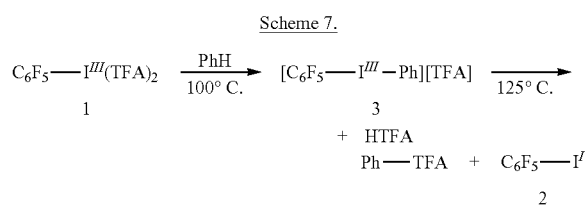

Example 2

This example demonstrates the use of an oxidizing electrophile comprising a main group element in oxidized form to activate and functionalize a C—H bond of the arene toluene.

The reactivity of toluene, which contains homolytically weak benzylic CH bonds, with $C_6F_5I^{(+3)}(TFA)_2$ (1) was studied. Using standard reaction conditions (e.g., 3 h, 150° C.), quantitative generation (based upon starting [1]) of p-MeC$_6$H$_4$TFA and o-MeC$_6$H$_4$TFA in a ~3:1 ratio was observed; with no formation of any benzylic oxy-functionalized products expected from a radical pathway (Scheme 8).

Scheme 8.

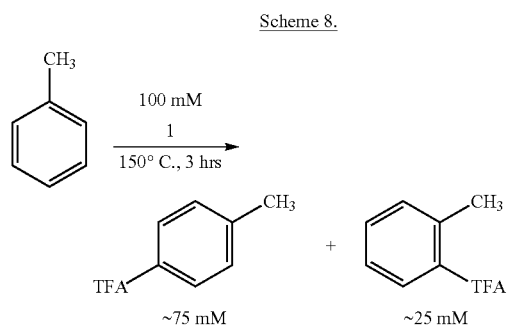

As is apparent, functionalization of the sp$^2$-hybridized carbon atom of the aryl ring was favored relative to functionalization of the sp$^3$-hybridized carbon atom of the methyl group.

Example 3

This example demonstrates the use of an oxidizing electrophile comprising a main group element in oxidized form to activate and functionalize a C—H bond of the arene benzene.

Pb(TFA)$_4$ was reacted with benzene (PhH) in trifluoroacetic acid (TFAH) at 25° C. to provide the selectively mono-functionalized product, PhTFA, in 80% yield (Scheme 9). The reaction was very facile as the reaction occurred nearly instantaneously at room temperature.

Scheme 9.

Example 4

This example demonstrates the use of an oxidizing electrophile comprising a main group element in oxidized form to activate and functionalize a C—H bond of the arene toluene.

The reactivity of toluene, which contains homolytically weak benzylic CH bonds, with Pb(TFA)$_4$ was studied. The mild reaction conditions (e.g., room temperature and TFAH) yielded exclusively the p-MeC$_6$H$_4$-TFA product (>95% yield) with no formation of any benzylic oxy-functionalized products expected from a radical pathway (Scheme 10).

Scheme 10.

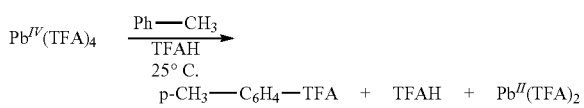

Example 5

This example demonstrates the use of an oxidizing electrophile comprising a main group element in oxidized form to activate and functionalize a C—H bond of the heteroalkane n-butyl trifluoroacetate.

Two small (3 mL) high pressure reactors with a glass inset liner and magnetic stir bar were each charged with 1.0 mL of a 250 mM solution of $C_6F_5$—I(TFA)$_2$ in 100 mM trifluoroacetic anhydride (TFAA)/trifluoroacetic acid (TFAH). To each reactor was also added 17 μL (17.3 mg, 0.1 mmol) of n-butyl trifluoroacetate. The reactors were pressure degassed eight times with 500 psig of argon; and then charged with 500 psig of argon and sealed. The reactors were then heated to 150° C. for three hours with stirring at 1000 rpm. Upon completion, the reactors were cooled to room temperature, and the pressure was released. Each solution was charged with 100 μL of a 31.32 mM solution of CH$_2$Cl$_2$ in TFAH as an internal standard; and the products were assessed by $^1$H-NMR. Analysis indicated the generation of 1,4-ditrifluoroacetoxybutane as the major product (5 mM, 5% yield) with the balance of material remaining as the starting material n-butyl trifluoroacetate.

Example 6

This example demonstrates the use of an oxidizing electrophile comprising a main group element in oxidized form to activate and functionalize a C—H bond of the heteroalkane n-butyl trifluoroacetate.

Two large (15 mL) high pressure reactors with a glass inset liner and magnetic stir bar were each charged with 2.0 mL of a 300 mM solution of Tl(TFA)$_3$ in TFAH. To each reactor was also added 0.1 mL (102 mg, 0.6 mmol, 1 eq relative to oxidant) of n-butyl trifluoroacetate. The reactors were pressure degassed five times with 500 psig of argon; and then charged with 500 psig of argon and sealed. The reactors were then heated to 180° C. for three hours with stirring at 1000 rpm. Upon completion, the reactors were cooled to room temperature, and the pressure was released. Each solution was charged with 0.2 ml of a 300 mM solution of $CH_2Cl_2$ in TFAH as an internal standard; and the products were assessed by $^1$H-NMR. Analysis indicated the generation of 1,4-ditrifluoroacetoxybutane as the major product (8 mM, 3% yield) with the balance of material remaining as the starting material n-butyl trifluoroacetate.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A process of preparing a functionalized compound, comprising:
   (a) providing a compound that is a heteroalkane or an arene,
   wherein
   the heteroalkane comprises at least one $sp^3$-hybridized carbon atom bearing a hydrogen atom and at least one heteroatom other than a carbon or hydrogen atom, and
   the arene comprises at least one $sp^2$-hybridized carbon atom bearing a hydrogen, and optionally comprising
   (i) one or more substituents comprising at least one $sp^3$-hybridized carbon atom,
   (ii) one or more heteroatoms to form a heteroarene and/or at least one substituent comprising a heteroatom, or
   (iii) both (i) and (ii),
   (b) contacting the compound with
   (i) an oxidizing electrophile comprising a main group element in oxidized form, wherein the main group element is selected from the group consisting of gallium, germanium, arsenic, selenium, bromine, indium, tin, antimony, tellurium, iodine, thallium, lead, and bismuth, or
   (ii) an oxidant and a reduced form of the oxidizing electrophile, to provide an initial reaction product, and
   (c) contacting the initial reaction product with a functionalized reactant selected from the group consisting of an oxygen acid, a nitrogen-containing functionalized reactant, a stannylation functionalized reactant, a sulfur-containing functionalized reactant, a formylation functionalized reactant, a phosphine functionalized reactant, a base, a carbonylation functionalized reactant, and a halogenation functionalized reactant, wherein a functionalized portion of the functionalized reactant replaces the main group element on the initial reaction product to provide the functionalized compound.

2. The process of claim 1, wherein step (b) comprises contacting the compound with an oxidizing electrophile comprising a main group element in oxidized form.

3. The process of claim 1, wherein step (b) comprises contacting the compound with an oxidant and a reduced form of the oxidizing electrophile.

4. The process of claim 1, wherein the oxidizing electrophile comprises thallium, lead, bismuth, antimony, selenium, tellurium, or a mixture thereof, each of which is in oxidized form.

5. The process of claim 4, wherein the oxidizing electrophile comprises thallium(III), lead(IV), bismuth(V), or Sb(V), or any mixture thereof.

6. The process of claim 1, wherein the oxidizing electrophile comprises iodine in oxidized form.

7. The process of claim 1, wherein the oxidizing electrophile is a salt that includes a counterion of the main group element in oxidized form, and wherein the counterion is a conjugate anion of an acid.

8. The process of claim 1, wherein the oxidizing electrophile is of formula $M^{+n}X_n$, wherein M is a metal or nonmetal main group element cation in an oxidation state of n, X is an anionic counterion, and n is the number of anionic charges necessary to balance the n+ positive charge of the metal ion.

9. The process of claim 1, wherein the oxidizing electrophile comprises one or more trifluoroacetate, acetate, sulfate, or alkylsulfonate anions.

10. The process of claim 1, wherein the contacting of step (b) takes place in an acidic medium.

11. The process of claim 10, wherein the acidic medium comprises a mineral acid, a carboxylic acid, a sulfonic acid, or any combination thereof.

12. The process of claim 1, further comprising separating the functionalized compound and an electrophile reduction product that is formed by the oxidizing electrophile.

13. The process of claim 12, further comprising contacting the separated electrophile reduction product and an oxidizing regeneration reagent to regenerate the oxidizing electrophile, wherein the oxidizing regeneration reagent preferably comprises hydrogen peroxide, oxygen, ozone, nitric acid, or a halogen.

14. The process of claim 13, wherein the electrophile reduction product and the oxidizing regeneration reagent are contacted in the presence of an oxidative regeneration catalyst, wherein the oxidative regeneration catalyst preferably comprises copper, silver, iron, or vanadium.

15. The process of claim 1, wherein the oxidizing electrophile comprising a main group element in oxidized form is present in less than stoichiometric quantities relative to the heteroalkane or arene and acts as a catalyst.

16. The process of claim 1, wherein a stoichiometric amount of the oxidizing electrophile reacts with the compound to form the initial reaction product.

17. The process of claim 1, wherein step (c) further comprises contacting the initial reaction product and functionalized reactant with water, an oxidant, or both.

18. The process of claim 1, wherein the functionalized reactant is selected from the group consisting of an oxygen acid, a hydrazine, a hydroxylamine, ammonia, a primary amine, a secondary amine, a stannous salt, octasulfur, alkylthiol, a phosphine, a weak base, formaldehyde, carbon monoxide, and a halide.

19. The process of claim 1, wherein the compound is a heteroalkane that is an alkyl monoester.

20. The process of claim 1, wherein the compound is an arene that comprises an aryl ring system or a heteroaryl ring system.

21. The process of claim 1, wherein the oxygen acid is trifluoroacetic acid, acetic acid, methanesulfonic acid, aqueous solutions thereof, or a combination thereof.

22. The process of claim 1, wherein the nitrogen-containing functionalized reactant is hydrazine, hydroxylamine, ammonia, a primary amine, or a secondary amine.

23. The process of claim 1, wherein the stannylation functionalized reactant is a stannous salt.

24. The process of claim 1, wherein the sulfur-containing functionalized reactant is octasulfur or an alkylthiol.

25. The process of claim 1, wherein the formylation functionalized reactant is formaldehyde.

26. The process of claim 1, wherein the phosphine functionalized reactant is a monosubstituted phosphine, disubstituted phosphine, or trisubstituted phosphine.

27. The process of claim 1, wherein the base is a conjugate base of acetate or trifluoroacetate.

28. The process of claim 1, wherein the carbonylation functionalized reactant is carbon monoxide.

29. The process of claim 1, wherein the halogenation functionalized reactant is a halide.

* * * * *